US012566117B2

(12) United States Patent
Pei et al.

(10) Patent No.: US 12,566,117 B2
(45) Date of Patent: Mar. 3, 2026

(54) DEVICE AND METHOD FOR SIMULATING AND TESTING SLUMP OF BACKFILL MATERIAL IN VERTICAL BOREHOLE OF CLOSED-LOOP

(71) Applicant: Guizhou University, Guiyang City (CN)

(72) Inventors: Peng Pei, Guiyang City (CN); Yumeng Wang, Guiyang City (CN); Yixia Chen, Guiyang City (CN); Fengqiang Deng, Guiyang City (CN)

(73) Assignee: Guizhou University, Guizhou Province (CN)

( * ) Notice: Subject to any disclaimer, the term of this patent is extended or adjusted under 35 U.S.C. 154(b) by 493 days.

(21) Appl. No.: 18/355,827

(22) Filed: Jul. 20, 2023

(65) Prior Publication Data

US 2024/0385092 A1     Nov. 21, 2024

(30) Foreign Application Priority Data

May 16, 2023     (CN) .......................... 202310544939.3

(51) Int. Cl.
*G01N 3/08* (2006.01)
*G06F 30/28* (2020.01)
*G01N 33/00* (2006.01)

(52) U.S. Cl.
CPC ............... *G01N 3/08* (2013.01); *G06F 30/28* (2020.01); *G01N 33/00* (2013.01); *Y02E 10/10* (2013.01)

(58) Field of Classification Search
None
See application file for complete search history.

(56) References Cited

U.S. PATENT DOCUMENTS

| | | | | |
|---|---|---|---|---|
| 4,854,175 A * | 8/1989 | Budhu | ..................... | G01N 3/24 |
| | | | | 73/841 |
| 2022/0178802 A1* | 6/2022 | Guo | ......................... | G01N 3/08 |
| 2022/0221384 A1* | 7/2022 | Hu | ........................... | G01N 3/08 |
| 2024/0337579 A1* | 10/2024 | Hu | .................... | G01N 15/0806 |
| 2024/0377300 A1* | 11/2024 | Yang | ..................... | G01N 33/24 |

* cited by examiner

*Primary Examiner* — Paul D Lee

(74) *Attorney, Agent, or Firm* — McHale & Slavin, P.A.

(57) ABSTRACT

Disclosed are a device and a method for simulating and testing slump of a backfill material in a vertical borehole of a closed-loop. The device includes a lower pipe body, an upper pipe body, a cushion layer, and a press platen. The lower pipe body and the upper pipe body are coaxial and have the same inner diameter. An upper end of the lower pipe body is provided with a first outer flange, a lower end of the upper pipe body is provided with a second outer flange, and the first outer flange is fixedly connected to the second outer flange. The cushion layer is disposed between the first outer flange and the second outer flange to form a gap between the first outer flange and the second outer flange for simulating a strata fracture.

10 Claims, 1 Drawing Sheet

DEVICE AND METHOD FOR SIMULATING AND TESTING SLUMP OF BACKFILL MATERIAL IN VERTICAL BOREHOLE OF CLOSED-LOOP

CROSS-REFERENCE TO RELATED APPLICATION

This application claims priority to Chinese Patent Application No. 2023105449393, filed on May 16, 2023 before China National Intellectual Property Administration, which is hereby incorporated by reference in its entirety.

TECHNICAL FIELD

The present disclosure relates to the technical field of geotechnical material experiments, in particular to a device and method for simulating and testing slump of a backfill material in vertical borehole of closed-loop.

BACKGROUND

Shallow geothermal energy is a highly competitive, green and low-carbon renewable energy source, and there is abundant shallow geothermal energy in Southwest China. However, due to the karstic landscape in Southwest China, there will be cross fractures net in the strata where the borehole is located, leading to different forms of slumping condition of the backfill material under various load pressures. These complex fractures net tend to have karstic water infiltration, which in turn affects the heat transfer of vertical loop. At present, some scholars have noticed that the heat transfer of vertical loop has an important relationship with fractures net as well as the slumping condition of backfill materials in boreholes, but there is no feasible test device and method to guide the slump of different backfill materials.

SUMMARY

An objective of the present disclosure is to provide a device and method for simulating and testing slump of a backfill material in a vertical borehole of closed-loop. Compared with the prior art, the condition of the fracture that the strata fracture crosses the borehole can be simulated through the device, and on this basis, a slumping condition of different backfill materials in the fracture can be tested.

In order to achieve the above objective, the present disclosure provides the following solution:

A device for simulating and testing slump of a backfill material in a vertical borehole of closed-loop disclosed by the present disclosure includes a lower pipe body, an upper pipe body, a cushion layer, and a press platen. The lower pipe body and the upper pipe body are coaxial and have the same inner diameter, so as to simulate a strata borehole through an inner hole of the lower pipe body and an inner hole of the upper pipe body. An upper end of the lower pipe body is provided with a first outer flange, a lower end of the upper pipe body is provided with a second outer flange, and the first outer flange is fixedly connected to the second outer flange. The cushion layer is disposed between the first outer flange and the second outer flange to form a gap between the first outer flange and the second outer flange for simulating a strata fracture, and the gap communicates with the inner hole of the lower pipe body and the inner hole of the upper pipe body simultaneously. The press platen has an outer profile matching the size of the inner hole of the lower pipe body, and thus the press platen can slide up and down in the lower pipe body and the upper pipe body to press a backfill material under the press platen.

Preferably, the device further includes a base fixed to the lower end of the lower pipe body.

Preferably, the cushion layer includes two backing plates, and the gap is located between the two backing plates.

Preferably, the first outer flange and the second outer flange are fixedly connected by bolts and nuts.

Preferably, screw rods of the bolts pass through the cushion layer to limit the cushion layer.

Preferably, both the lower tube body and the upper tube body are made of transparent material.

Preferably, a plurality of cushion layers capable of being replaced with each other are provided, and the plurality of cushion layers have different thicknesses.

A method for simulating and testing slump of a backfill material in a vertical borehole of a closed-loop is further disclosed by the present disclosure. The method uses the device for simulating and testing the slump of a backfill material in a vertical borehole of a closed-loop, and includes the following steps.

Step 1: measuring multiple groups of density data of backfill sands using a cutting ring method, and setting an average value of all data as an approximate value p of the density of the backfill sands;

Step 2: based on a backfill sands which is collected on site, simulating a vertical load on the backfill sands at a certain position by using a total gravity of overburden backfill sands without considering a friction force between the backfill sands inside a borehole and an inner wall of the borehole, setting up an experiment to simulate a slumping condition of the backfill sands with different apertures in a fracture at a depth h, where the cross-sectional area of the borehole is $S=\pi r^2$, a pressure at a corresponding depth is $P=\rho gh$, and a load to be applied is $F=PS=\rho ghS$, and calculating the total gravity of the required overburden backfill sands according to above formula;

Step 3: injecting the backfill sands to be measured from an upper end of an upper pipe body until the upper pipe body and the lower pipe body are filled with the backfill sands, observing and measuring a spreading condition of the backfill sands under a natural falling state, recording spread length and width, and calculating a slumping area;

Step 4: smoothing an upper part of the backfill sands in the simulated borehole, and horizontally placing the lower surface of a press platen at a center of a surface layer of the backfill sands; and applying a predetermined downward pressure to the press platen and maintaining the predetermined pressure, observing and measuring the spreading condition of the backfill sands, recording the spread length and width, and calculating the slumping area;

Step 5: remaining the predetermined pressure unchanged, observing and measuring a spreading condition of the backfill sands at an interval of a predetermined time, recording the spread length and width, and calculating the slumping area;

Step 6: pouring out the backfill sands in the upper pipe body and the lower pipe body; remaining the thickness of a cushion layer and a backfill sands material unchanged, changing the size of h, repeating Step 2 to Step 5, and measuring a slumping condition of the same backfill material with the same aperture and different borehole depths;

Step 7: pouring out the backfill sands in the upper pipe body and the lower pipe body; remaining the h and backfill sands material unchanged, changing the thickness of the cushion layer, repeating Step 2 to Step 5, and measuring a slumping condition of the same backfill material with the same borehole depth but different apertures; and Step 8: pouring out the backfill sands in the upper pipe body and the lower pipe body; changing the backfill sands material, remaining the h and the thickness of the cushion layer unchanged, repeating Step 1 to Step 5, and measuring a slumping condition of different backfill materials with the same aperture and the same bore depth.

Preferably, in step 4, the pressure is applied by a uniaxial testing machine to the press platen.

Preferably, in step 5, the predetermined time is 15 minutes.

Compared with the prior art, the present disclosure has the following technical effects:

In accordance with the device and method disclosed by the present disclosure, on the one hand, the slumping conditions of the same backfill material in the same aperture with different depth loads can be simulated, so that a relationship between the slump and the load is obtained. On the other hand, the slumping conditions of the same backfill material in different apertures under the same overhead load can be simulated, so that a relationship between the slump and the aperture is obtained. The slumping conditions of different granular backfill materials with the same aperture and the same overhead load can also be simulated, so that a relationship between the slump and different granular backfill materials is obtained.

Therefore, the problem that there is no experimental device for testing the slump of a backfill material in a borehole in the prior art is solved. The device is simple in structure, and is of important significance for guiding the output of a novel reliable backfill material as well as the backfilling method at the fracture.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

Figure 1:
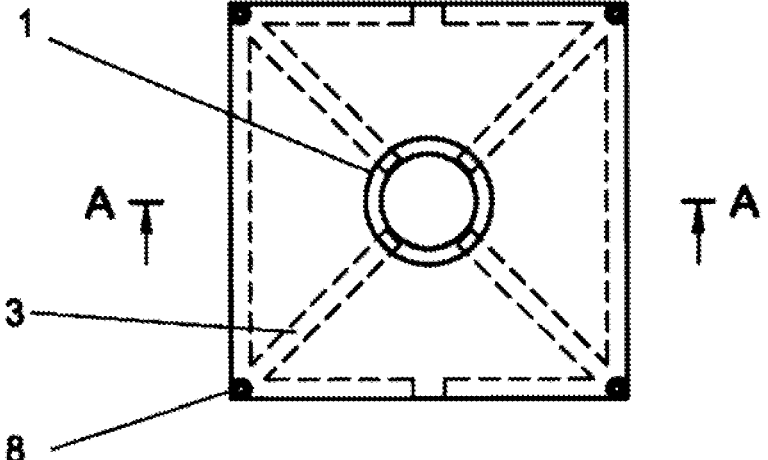
FIG. 1 is a schematic diagram of a device for simulating and testing slump of a backfill material in a vertical borehole of a closed-loop in accordance with the embodiments of the present disclosure in an overhead direction.

In the drawings: 1—upper pipe body; 2—second outer flange; 3—cushion layer; 4—first outer flange; 5—lower pipe body; 6—base; 7—pressure table; 8—bolt.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

An objective of the present disclosure is to provide a device and method for simulating and testing slump of a backfill material in a vertical borehole of a closed-loop. Compared with the prior art, the condition of the fracture that the strata fracture crosses the borehole can be simulated through the device, and on this basis, slumping conditions of different backfill materials in the fracture can be tested.

To make the objectives, features and advantages of the present disclosure more apparently and understandably, the following further describes the present disclosure in detail with reference to the accompanying drawings and the specific embodiments.

Figure 2:
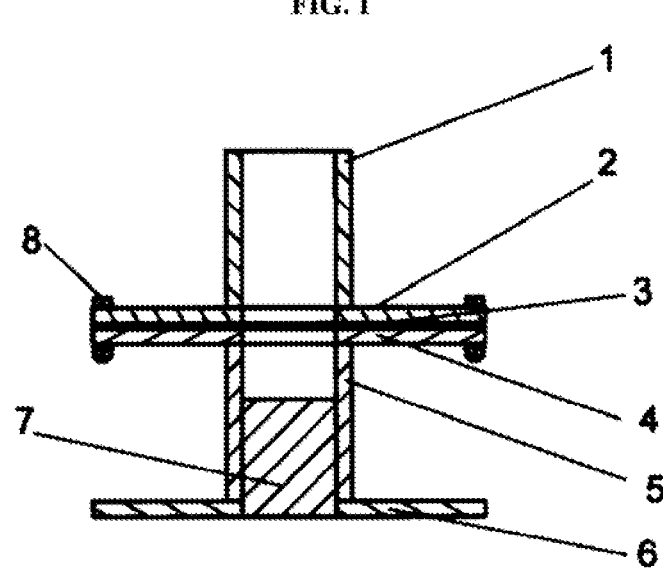
FIG. 2 is a sectional view of FIG. 1 in an A-A direction.

Referring to FIG. 1 to FIG. 2, a device for simulating and testing slump of a backfill material in a vertical borehole of a closed-loop (hereinafter referred to as a simulation test device) is provided in accordance with the embodiment. The device includes a lower pipe body 5, an upper pipe body 1, a cushion layer 3, and a press platen 7.

The lower pipe body 5 and the upper pipe body 1 are coaxial and have the same inner diameter, so as to simulate a strata borehole through an inner hole of the lower pipe body 5 and an inner hole of the upper pipe body 1. The simulated strata borehole in this embodiment is a vertical hole. An upper end of the lower pipe body 5 is provided with a first outer flange 4, a lower end of the upper pipe body 1 is provided with a second outer flange 2, and the first outer flange 4 is fixedly connected to the second outer flange 2, such that the inner hole of the lower pipe body 5 and the inner hole of the upper pipe body 1 cannot be staggered from each other. The cushion layer 3 is disposed between the first outer flange 4 and the second outer flange 2 to form a gap between the first outer flange 4 and the second outer flange 2 for simulating a strata fracture. The gap communicates with the inner hole of the lower pipe body 5 and the inner hole of the upper pipe body 1.

The working principle of the simulation test device of this embodiment is described as follows.

Due to the existence of the strata fracture, the strata borehole is divided into upper and lower parts by the strata fracture. In this embodiment, the gap between the first outer flange 4 and the second outer flange 2 is used to simulate the strata fracture, the inner hole of the upper pipe body 1 is used to simulate the upper part of the strata borehole, and the inner hole of the lower pipe body 5 is used to simulate the lower part of the strata borehole.

As a possible example, in this embodiment, the press platen 7 has an outer profile which is matched with a size of the inner hole of the lower pipe body 5, such that the press platen 7 can slide up and down in the lower pipe body 5 and the upper pipe body 1 to press the backfill material under the press platen 7. In this embodiment, clearance fit is preferred between the press platen 7 and the inner hole of the upper pipe body 1, and between the press platen 7 and the inner hole of the lower pipe body 5, so as to ensure that the press platen 7 can move up and down conveniently when pressing the whole surface layer of the backfill material.

As a possible example, in the present embodiment, the simulation test device further includes a base 6 which is fixed to the lower end of the lower pipe body 5. The base 6 can be placed on the ground or on a workbench to improve the stability of the simulation test device. Specifically, in this embodiment, the base 6 is a square plate, and the axis of the lower pipe body 5 perpendicularly passes through the geometric center of the base 6. Depending on actual needs, the base 6 may also be of other types, such as a circular plate.

As a possible example, in this embodiment, the cushion layer 3 includes two backing plates, and the gap is located between the two backing plates. Specifically, the two backing plates are arranged symmetrically with respect to the longitudinal section of the upper pipe body 1. Each backing plate includes two radial plates, two outer plates and a middle plate. The two radial plates are arranged along a radial direction of the upper pipe body 1 and are perpendicular to each other. Both ends of the middle plate are respectively connected to the ends, deviating from the axis of the upper pipe body 1, of the two radial plates. The ends, far away from the axis of the upper pipe body 1, of the outer plates are connected to the ends of the middle plate, and the two outer plates are respectively connected to both ends of the middle plate. Depending on actual needs, the cushion layer 3 may also be of other types. For example, the cushion layer 3 is an integral square plate, and the cushion layer 3 is provided with a through hole coaxial with the lower pipe body 5, and the diameter of the through hole is greater than the inner diameter of the lower pipe body 5, thus making the gap annular.

As a possible example, in this embodiment, the first outer flange 4 and the second outer flange 2 are fixedly connected by bolts 8 and nuts, and screw rods of the bolt 8 pass through the second outer flange 2 and the first outer flange 4 in turn and then are threaded with the nuts. Depending on actual needs, the first outer flange 4 may be fixedly connected to the second outer flange 2 in other ways by those skilled in the art.

As a possible example, in this embodiment, the screw rods of the bolts 8 pass through the cushion layer 3 to limit the cushion layer 3. Depending on actual needs, the movement of the cushion layer 3 can be limited by clamping the cushion layer 3 with the first outer flange 4 and the second outer flange 2 by those skilled in the art.

As a possible example, in this embodiment, the first outer flange 4 and the second outer flange 2 are both square flanges, and the positions of the two flanges are opposite. There are four bolts 8. The four bolts 8 are respectively mounted at four right angles of the first outer flange 4 and are threaded to corresponding nuts. Two bolts 8 pass through both ends of the middle plate of one of the backing plates, and the other two bolts 8 pass through both ends of the middle plate of the other backing plate.

As a possible example, in this embodiment, both the lower tube body 5 and the upper tube body 1 are made of transparent material, so as to facilitate observation of internal conditions.

As a possible example, in this embodiment, a plurality of cushion layers 3 capable of being replaced with each other are provided, and the plurality of cushion layers have different thicknesses. Depending on actual needs, the cushion layer 3 with the corresponding thickness can be employed.

As a possible example, in this embodiment, the backing plate has a length of 600 mm and a width of 250 mm, and the cushion layer has a thickness from 0.5 mm to 2.5 mm. The inner diameter of a cylinder part of the upper pipe body 1 is from 100 mm to 140 mm, a wall thickness of the cylinder part of the upper pipe body 1 is not less than 5 mm, and a depth of the cylinder part of the upper pipe body 1 is 200 mm. The thickness of each of the first outer flange 4 and the second outer flange 2 is not less than 3 mm, and the length and width of each of the first outer flange 4 and the second outer flange 2 are 600 mm. The size of the cylindrical part of the lower pipe body 5 is the same as that of the cylindrical part of the upper pipe body 1. Both the length and width of the base 6 are not less than 600 mm, the outer diameter of each bolt 8 is from 5 mm to 10 mm, and the height of the press platen 7 is 150 mm. Depending on actual needs, other size may be selected by those skilled in the art.

A method for simulating and testing slump of a backfill material in a vertical borehole of a closed-loop (hereinafter referred to as a simulation test method) is disclosed by the present disclosure. The method uses the simulation test device and includes the following steps:

Step 1: Multiple groups of density data of backfill sands are measured by using a cutting ring method, and an average value of all data is set as an approximate value ρ of the density of the backfill sands. In this embodiment, the size of a cutting ring is diameter (φ)70 mm×height (H) 52 mm, a total of ten groups of data is measured, and the approximate value ρ of the density of the backfill sands reserves two decimal fractions. It should be noted that, during actual backfilling, the density of the backfill sands at a certain depth is mainly affected by a pressure of backfill sands above and a friction force between the backfill sands and a borehole wall, and the actual density is not a stable value. During the experiment, the approximate value measured after the backfill sands collected on site is pressed in the ring knife is adopted, and this density is used to equivalently calculate an overburden load of the backfill sands at different depths as the basis of applying pressure.

Step 2: Based on backfill sands collected on site, simulating a vertical load on the backfill sands at a certain position by using a total gravity of overburden backfill sands without considering a friction force between the backfill sands inside a borehole and an inner wall of the borehole. The simulating in an experiment is set. An experiment is set up to simulate a slumping condition of the backfill sands with different apertures in a fracture at a depth h, where a cross-sectional area of the borehole is $S=\pi r^2$, a pressure at the corresponding depth position is $P=\rho gh$ and a load to be applied is $F=PS=\rho ghS$; and the total gravity of the required overburden backfill sands is calculated according to the above formula, and the result is rounded to the nearest integer.

Step 3: The backfill sands to be measured is injected from an upper end of an upper pipe body 1 until the upper pipe body 1 and the lower pipe body 5 are full of the backfill sands, a spreading condition (the backfill sands is spread in the gap for simulating the strata fracture) of the backfill sands under a natural falling state is observed and measured, the spread length and width are recorded, and a slumping area (the slumping area is a spreading area of the backfill sands in the gap) is calculated. The length, width and slumping area are all rounded to nearest integers, and the data of the same type in the following steps is also rounded to the nearest integer. Specifically, in this embodiment, the simulation test device is placed on the center of the table below a uniaxial testing machine for operation, so as to facilitate the subsequent pressing operation of a press platen 7 by the uniaxial testing machine.

Step 4: The upper part of the backfill sands in the simulated borehole is smoothed, and the lower surface of a press platen is placed at the center of a surface layer of the backfill sands. A preset downward pressure is applied to the press platen and the predetermined pressure is maintained (the predetermined pressure is the total gravity calculated in Step 1, a spreading condition of the backfill sands is observed and measured, the spread length and width are recorded, and a slumping area is calculated. Since the uniaxial testing machine is used for pressing down in this embodiment, a predetermined pressure value can be set through a control panel of the uniaxial testing machine, and the time for holding the predetermined pressure later can be set.

Step 5: The predetermined pressure remains unchanged, and a spreading condition of the backfill sands is observed and measured at an interval of a predetermined time, the spread length and width are recorded, and a slumping area is calculated. In this embodiment, the predetermined time is 15 minutes.

Step 6: The backfill sands in the upper pipe body 1 and the lower pipe body 5 are poured out. The thickness of a cushion layer 3 and a backfill sands material remain unchanged, the size of h is changed, and then Step 2 to Step 5 are repeated. The slumping condition of the same backfill material with the same aperture and different borehole depths is measured.

Step 7: The backfill sands in the upper pipe body 1 and the lower pipe body 5 are poured. The h and the backfill sands material remain unchanged, the thickness of the cushion layer 3 is changed, and Step 2 to Step 5 are repeated. The slumping condition of the same backfill material with the same borehole depth and different facture widths is measured.

Step 8: The backfill sands in the upper pipe body 1 and the lower pipe body 5 are poured out. The backfill sands material is changed, the h and the thickness of the cushion layer remain unchanged, and then Step 1 to Step 5 are repeated. The slumping condition of different backfill materials at the same aperture and the same borehole depth is measured.

The stimulation test method of this embodiment uses the simulation test device above, on the one hand, the slumping conditions of the same backfill material in the same aperture with different depth loads can be simulated, so that a relationship between the slump and the load is obtained. On the other hand, the slumping conditions of the same backfill material in different apertures under the same overhead load can be simulated, so that a relationship between the slump and the aperture is obtained. The slumping conditions of different granular backfill materials under the same aperture and the same overhead load can also be simulated, so that a relationship between the slump and different granular backfill materials is obtained.

Several examples are used for illustration of the principles and implementation methods of the present disclosure. The description of the embodiments is merely used to help illustrate the method and its core principles of the present disclosure. In addition, those of ordinary skill in the art can make various modifications in terms of specific embodiments and scope of application in accordance with the teachings of the present disclosure. In conclusion, the content of this specification shall not be construed as a limitation to the present disclosure.

What is claimed is:

1. A device for simulating and testing slump of a backfill material in a vertical borehole of a closed-loop, comprising a lower pipe body, an upper pipe body, a cushion layer, and a press platen, wherein the lower pipe body and the upper pipe body are coaxial and have the same inner diameter, so as to simulate a strata borehole through an inner hole of the lower pipe body and an inner hole of the upper pipe body; an upper end of the lower pipe body is provided with a first outer flange, a lower end of the upper pipe body is provided with a second outer flange, and the first outer flange is fixedly connected to the second outer flange;

wherein the cushion layer is disposed between the first outer flange and the second outer flange to form a gap between the first outer flange and the second outer flange for simulating a strata fracture; the gap communicates with the inner hole of the lower pipe body and the inner hole of the upper pipe body simultaneously; and wherein the press platen has an outer profile which is matched with a size of the inner hole of the lower pipe body, so that the press platen is able to slide up and down in the lower pipe body and the upper pipe body to press the backfill material under the press platen.

2. The device for simulating and testing slump of a backfill material in a vertical borehole of a closed-loop according to claim 1, further comprising a base, wherein the base is fixed to a lower end of the lower pipe body.

3. The device for simulating and testing slump of a backfill material in a vertical borehole for a closed-loop according to claim 1, wherein the cushion layer comprises two backing plates, and the gap is located between the two backing plates.

4. The device for simulating and testing slump of a backfill material in a vertical borehole of a closed-loop according to claim 1, wherein the first outer flange and the second outer flange are fixedly connected by bolts and nuts.

5. The device for simulating and testing slump of a backfill material in a vertical borehole of a closed-loop according to claim 4, wherein screw rods of the bolts pass through the cushion layer to limit the cushion layer.

6. The device for simulating and testing slump of a backfill material in a vertical borehole of a closed-loop according to claim 1, wherein both the lower pipe body and the upper pipe body are made of transparent material.

7. The device for simulating and testing slump of a backfill material in a vertical borehole of a closed-loop according to claim 1, wherein a plurality of cushion layers capable of being replaced with each other are provided, and the plurality of cushion layers have different thicknesses.

8. A method for simulating and testing slump of a backfill material in a vertical borehole of a closed-loop, using the device for simulating and testing the slump of a backfill material in a vertical borehole of a closed-loop according to claim 1, and comprising the following steps:

step 1: measuring a plurality of groups of density data of backfill sands using a cutting ring method, and setting an average value of all data as an approximate value ρ of the density of the backfill sands;

step 2: based on a backfill sands which is collected on site, simulating a vertical load on the backfill sands at a certain position by using a total gravity of overburden backfill sands without considering a friction force between the backfill sands inside a borehole and an inner wall of the borehole; setting up an experiment to simulate a slumping condition of the backfill sands with different apertures in a fracture at a depth h, wherein the cross-sectional area of the borehole is $S=\pi r^2$, a pressure at a corresponding depth is $P=\rho gh$, and a load to be applied is $F=PS=\rho ghS$; and calculating a total gravity of the required overburden backfill sands according to above formula;

step 3: injecting the backfill sands to be measured from an upper end of an upper pipe body until the upper pipe body and the lower pipe body are filled with the backfill sands, observing and measuring a spreading condition of the backfill sands under a natural falling state, recording spread length and width, and calculating a slumping area;

step 4: smoothing an upper part of the backfill sands in the simulated borehole, and horizontally placing the lower surface of a press platen at a center of a surface layer of the backfill sands; and applying a predetermined downward pressure to the press platen and maintaining the predetermined pressure, observing and measuring the spreading condition of the backfill sands, recording the spread length and width, and calculating the slumping area;

step 5: while the predetermined pressure remains unchanged, observing and measuring the spreading condition of the backfill sands at an interval of a predetermined time, recording the spread length and width, and calculating the slumping area;

step 6: pouring out the backfill sands in the upper pipe body and the lower pipe body; while the thickness of a cushion layer and a backfill sands material remain unchanged, changing the depth of h, repeating step 2 to step 5, and measuring slumping conditions of the same backfill material with a same aperture and different borehole depths;

step 7: pouring out the backfill sands in the upper pipe body and the lower pipe body; while the depth h and backfill sands material remain unchanged, changing the thickness of the cushion layer, repeating step 2 to step 5, and measuring slumping conditions of the same backfill material with a same borehole depth and different apertures; and step 8: pouring out the backfill sands in the upper pipe body and the lower pipe body; changing the backfill sands material, while the depth h and the thickness of the cushion layer remain unchanged, repeating step 1 to step 5, and measuring slumping conditions of different backfill materials with a same aperture and a same bore depth.

9. The method for simulating and testing slump of a backfill material in a vertical borehole of a closed-loop according to claim 8, wherein in step 4, the pressure is applied by a uniaxial testing machine to the press platen.

10. The method for simulating and testing slump of a backfill material in a vertical borehole of a closed-loop according to claim 8, wherein in step 5, the predetermined time is 15 minutes.

* * * * *